United States Patent
Pfirrmann

(10) Patent No.: US 6,821,968 B2
(45) Date of Patent: Nov. 23, 2004

(54) STABLE TAUROLIDINE ELECTROLYTE SOLUTIONS

(75) Inventor: Rolf W. Pfirrmann, Lucerne (CH)

(73) Assignee: Ed. Geistlich Soehne AG fuer chemische Industrie, Wolhusen (CH)

( * ) Notice: Subject to any disclaimer, the term of this patent is extended or adjusted under 35 U.S.C. 154(b) by 0 days.

(21) Appl. No.: 10/253,907

(22) Filed: Sep. 25, 2002

(65) Prior Publication Data

US 2003/0066753 A1 Apr. 10, 2003

Related U.S. Application Data

(60) Provisional application No. 60/324,533, filed on Sep. 26, 2001.

(51) Int. Cl.⁷ ............................................... A61K 31/54
(52) U.S. Cl. ............................ 514/222.5; 514/772.5; 514/922; 514/970
(58) Field of Search ............................. 514/222.5, 922, 514/970, 772.5

(56) References Cited

U.S. PATENT DOCUMENTS

| | | |
|---|---|---|
| 4,350,156 A | 9/1982 | Malchesky et al. |
| 4,626,536 A | 12/1986 | Pfirrmann |
| 5,889,183 A | 3/1999 | Herdeis et al. |
| 6,080,397 A | 6/2000 | Pfirrmann |

FOREIGN PATENT DOCUMENTS

| | | |
|---|---|---|
| DE | 35 36 560 A1 | 4/1986 |
| EP | 0 139 535 A2 | 5/1985 |
| EP | 0 147 021 A1 | 7/1985 |
| EP | 0 253 662 A1 | 1/1988 |
| EP | 1 040 841 A1 | 10/2000 |
| EP | 1 247 524 A1 | 10/2002 |
| GB | 2 165 752 A | 4/1986 |

OTHER PUBLICATIONS

Fiedler, Dr. Herbert P., "Lexikon der Hilfsstoffe für Pharmazie, Kosmetik und Angrenzende Gebiete", *Editio Canter Aulendorf*, pp. 695 (1985).

Janik, Joseph S., et al., "Prevention of Postoperative Peritoneal Adhesions, Efficacy of Povidone", *Arch Surg.*, vol. 117, pp. 1321–1324, (1982).

Kopple, JD, et al., "Effect of Intravenous Taurine Supplementation on Plasma, Blood Cell, and Urine Taurine Concentrations in Adults Undergoing Long–term Parenteral Nutrition", *Am. J. Clin. Nutr.*, vol. 52, No. 5., (1990) *Abstract*.

Stapleton, P. P., et al., "Taurine and Human Nutrition", *Clinical Nutrition*, vol. 16, pp. 103–107, (1997).

Wicki et al., "Taurolin—A New Concept in Antimicrobial Chemotherapy in Surgical Infection", *Urban & Scwarzenberg*, vol. III, pp. 244–253 (1985).

Kirsch, L., et al., "The Effect of Polyvinylpyrrolidine on the Stability of Taurolidine", *Pharmaceutical Development and Technology*, 2:4, 345–356 (1997).

*Primary Examiner*—Frederick Krass
(74) *Attorney, Agent, or Firm*—Rothwell, Figg, Ernst & Manbeck, PC

(57) ABSTRACT

A taurolidine composition includes an aqueous solution containing about 1.5–3% by weight taurolidine, the solution containing a stability-enhancing effective amount of at least one physiologically acceptable electrolyte, such that the solution is substantially isotonic.

19 Claims, No Drawings

STABLE TAUROLIDINE ELECTROLYTE SOLUTIONS

CROSS-REFERENCE TO RELATED APPLICATION

This application claims the benefit of U.S. Provisional Application Ser. No. 60/324,533 filed Sep. 26, 2001.

FIELD OF THE INVENTION

The present invention relates to taurolidine solutions.

DESCRIPTION OF THE BACKGROUND ART

Although taurolidine 1% solutions have been prepared with electrolyte-containing solutions such as ringer solution, there previously has been no suggestion of taurolidine at concentrations greater than 1% in electrolyte solutions such as ringer solution.

Known taurolidine solutions at higher concentrations, e.g., known 2% taurolidine solutions, previously have sometimes had stability problems. For example, droplets clinging on the inside of bottles of 2% taurolidine solution sometimes dry and form crystals, resulting in undesirable particles in the solution. Prior methods for avoiding such problems include storing bottles horizontally on their sides so that droplets do not form in the bottles, and not storing the solutions under refrigeration. However, it is desirable to have bottles of solution which do not require special storage orientation, and which can be refrigerated to extend the shelf-life.

There remains a need in the art for taurolidine solutions having greater stability.

SUMMARY OF THE INVENTION

In accordance with the present invention, a taurolidine composition includes an aqueous solution containing about 1.5–3% by weight taurolidine, the solution containing a stability-enhancing effective amount of at least one physiologically acceptable electrolyte which is present at a concentration sufficient to render said solution substantially isotonic.

DESCRIPTION OF THE PREFERRED EMBODIMENTS

The present invention solves the prior stability problems of higher concentration taurolidine solutions by providing stable aqueous solutions containing taurolidine at a concentration within the range of about 1.5–3% by weight. The solutions are rendered stable by including therein a stability-enhancing effective amount of at least one physiologically acceptable electrolyte so that the resulting solution is substantially isotonic. Suitable electrolyte(s) provide ions selected from the group consisting of $Na^+$, $K^+$, $Mg^{++}$, $Cl^-$, $H_2PO_4^-$, $Acetate^-$, $HCO_3^-$, and mixtures thereof. In preferred embodiments, the electrolyte(s) are selected from the group consisting of NaCl, KCl, $CaCl_2$, $NaHCO_3$, and mixtures thereof.

In preferred embodiments, taurolidine is present in the solution within a range of about 1.5–2.5% by weight, more preferably within the range of about 1.7–2.3% by weight, even more preferably within the range of about 1.8–2.2% by weight, still more preferably within the range of about 1.9–2.1% by weight, most preferably about 2% by weight.

For example, one composition in accordance with the present invention comprises an isotonic ringer solution including about 2% by weight taurolidine. An alternative to use of ringer solution is full electrolyte solution, which contains phosphates not present in ringer solution.

In particularly preferred embodiments, a composition in accordance with the present invention additionally includes sufficient physiologically acceptable colloidal material (colloid) so as to also effectively render the inventive solution iso-oncotic. The colloidal material can be polyvinylpyrrolidone (PVP), hydroxy ethyl starch (HES), or the like. Preferred colloidal materials include low molecular weight PVP, having an average molecular weight within the range of about 1,000–15,000, preferably within the range of about 1,000–13,000, more preferably about 9,000. A particularly preferred PVP for use in accordance with the present invention is Kollidon or Povidone. Preferred amounts of colloidal material in the solution are within the range of about 1–10% by weight, preferably about 3–7% by weight, most preferably about 5% by weight.

One preferred solution in accordance with the present invention includes the following in percentages by weight in water for injection:

2% taurolidine
5% Kollidon
0.4% NaCl
0.005% KCl
0.0066% $CaCl_2$
0.005% $NaHCO_3$ Isotonic taurolidine solutions in accordance with the present invention also can be prepared so as to include at least one amino acid, wherein the amounts of other electrolytes added to the solution are reduced in proportion to the amount of the one or more amino acid(s) added, so as to maintain isotonicity. Preferred amounts of amino acid(s) in the solution are within the range of about 0.1–3% by weight, more preferably within the range of about 0.2–2% by weight, still more preferably within the range of about 0.3–1% by weight, even more preferably within the range of about 0.4–0.6% by weight, most preferably about 0.5% by weight. Taurine is particularly preferred. One exemplary composition in accordance with this embodiment, in water for injection, is as follows in percentages by weight:

2% taurolidine
5% Kollidon
0.5% taurine
0.26% NaCl
0.0033% KCl
0.004% $CaCl_2$
0.003% $NaHCO_3$ Solutions in accordance with the invention have a pH within the range of about 7.1–7.9. The above solution before sterilization has a pH of about 7.8, and after sterilization has a pH of about 7.2–7.38. Ideally, a solution in accordance with the present invention has a pH of about 7.4.

In yet another embodiment, taurultam is substituted for amino acid(s) such as taurine in isotonic taurolidine solutions according to the invention. For example, about 0.1–1% by weight taurultam may be substituted for amino acid(s) such as taurine in isotonic 1.5–3% taurolidine solutions, preferably about 0.2–0.5% by weight taurultam.

The present invention also is applicable to methods for preparing the compositions as described above. For example, the invention includes methods for stabilizing solutions of taurolidine within the range of about 1.5–3% by weight, comprising preparing a solution containing about 1.5–3% taurolidine and a substantially isotonic solution-forming amount of at least one physiologically acceptable electrolyte so as to form a substantially isotonic solution. In preferred embodiments, a physiologically acceptable colloidal material is added to the solution so as to render the solution substantially iso-oncotic.

What is claimed is:

1. A taurolidine composition comprising an aqueous solution containing about 1.5–3% by weight taurolidine based on the amount of water present in said solution, said solution containing at least one physiologically acceptable electrolyte, which is present at a concentration sufficient to render said solution isotonic and stable to crystal formation when the solution is stored in a bottle under conditions subject to droplet formation on an internal surface of said bottle.

2. The composition of claim 1 wherein said solution contains a plurality of physiologically acceptable electrolytes.

3. The composition of claim 2 wherein said electrolytes provide ions selected from the group consisting of Na+, K+, Mg++, Cl−, H2PO4−, Acetate−, HCO3−, and mixtures thereof.

4. The composition of claim 2 wherein said electrolytes are selected from the group consisting of NaCl, KCl, CaCl2, NaHCO3, and mixtures thereof.

5. The method of claim 2 wherein said solution contains about 1.7–2.3% by weight taurolidine.

6. The composition of claim 2 wherein said solution contains about 1.8–2.2% by weight taurolidine.

7. The composition of claim 2 wherein said solution contains about 1.9–2.1% by weight taurolidine.

8. The composition of claim 2 wherein said solution contains about 2% by weight taurolidine.

9. The composition of claim 2 wherein said solution further contains an amount of a colloid effective to render said solution iso-oncotic.

10. The composition of claim 9 wherein said colloid is present in said solution in an amount of about 1–10% by weight based on the amount of water present in said solution.

11. The composition of claim 10 wherein said colloid comprises PVP having a molecular weight in the range of about 1,000–15,000.

12. The composition of claim 11 wherein said molecular weight Is about 9.000.

13. The composition of claim 2 wherein said solution further includes about 0.1–3% by weight of at least one amino acid based on the amount of water present in said solution.

14. The composition of claim 13 wherein said at least one amino acid is taurine.

15. The composition of claim 14 wherein said solution contains about 0.3–1% by weight taurine.

16. The composition of claim 15 wherein said solution contains about 0.4–0.6% by weight taurine.

17. The composition of claim 16 wherein said solution contains about 0.5% by weight taurine.

18. The composition of claim 2 where said solution further includes about 0.1–1% by weight taurultam based on the amount water present in said solution.

19. The composition of claim 18, wherein said solution contains about 0.2–0.5% by weight taurultam.

* * * * *